(12) United States Patent  (10) Patent No.: US 8,647,121 B1
Witlin et al.  (45) Date of Patent: Feb. 11, 2014

(54) FOOD ITEM GRADING

(75) Inventors: Brian Benjamin Witlin, Mountain View, CA (US); Michelle Sau Kuen Lee, San Francisco, CA (US); Scott Golubock, Morgan Hill, CA (US); Maria Redin, San Francisco, CA (US)

(73) Assignee: YottaMark, Inc., Redwood City, CA (US)

( * ) Notice: Subject to any disclaimer, the term of this patent is extended or adjusted under 35 U.S.C. 154(b) by 927 days.

(21) Appl. No.: 12/581,834

(22) Filed: Oct. 19, 2009

Related U.S. Application Data

(60) Provisional application No. 61/106,487, filed on Oct. 17, 2008, provisional application No. 61/109,868, filed on Oct. 30, 2008, provisional application No. 61/251,692, filed on Oct. 14, 2009.

(51) Int. Cl.
*G09B 19/00* (2006.01)
(52) U.S. Cl.
USPC .......................................................... 434/127
(58) Field of Classification Search
USPC .......................................................... 434/127
See application file for complete search history.

(56) References Cited

U.S. PATENT DOCUMENTS

| 4,650,218 | A | 3/1987 | Hawke | |
| 6,305,942 | B1 * | 10/2001 | Block et al. | 434/156 |
| 2003/0165799 | A1 * | 9/2003 | Bisogno | 434/127 |
| 2003/0171944 | A1 * | 9/2003 | Fine et al. | 705/1 |
| 2005/0113649 | A1 | 5/2005 | Bergantino | |
| 2006/0074716 | A1 * | 4/2006 | Tilles et al. | 705/2 |
| 2006/0199155 | A1 | 9/2006 | Mosher | |
| 2007/0118357 | A1 * | 5/2007 | Kasravi et al. | 704/10 |
| 2008/0083825 | A1 * | 4/2008 | Yang et al. | 235/375 |
| 2009/0006127 | A1 * | 1/2009 | Bahar | 705/2 |
| 2009/0164466 | A1 * | 6/2009 | Badyal | 707/7 |
| 2009/0275002 | A1 * | 11/2009 | Hoggle | 434/127 |
| 2010/0124359 | A1 * | 5/2010 | Vaidya | 382/103 |
| 2010/0292998 | A1 * | 11/2010 | Bodlaender et al. | 705/2 |

OTHER PUBLICATIONS

U.S. Appl. No. 12/581,827 non-final Office action, mailed Mar. 29, 2012.
U.S. Appl. No. 12/581,827 Applicants' response, submitted Oct. 1, 2012.
U.S. Appl. No. 12/581,827 final Office action, mailed Jun. 7, 2013.
U.S. Appl. No. 13/785,617, filed Oct. 19, 2009, Brian Witlin, Food Item Selection.

* cited by examiner

*Primary Examiner* — Sam Yao
*Assistant Examiner* — Jerry-Daryl Fletcher
(74) *Attorney, Agent, or Firm* — Peters Verny, LLP

(57) ABSTRACT

Systems and methods of grading food items include a user customizable profile that allows a user to specify nutritional needs, dietary goals, or a medical state. The user profile is used to provide a user specific grade to one or more food items. This grade is configured for a user to compare food items and learn which provides better nutrition according to their profile. The user profile is optionally configured to take into account a medical state such as celiac disease, diabetes, or a nutritional deficiency. A grade can be provided for a single food item or to a list of food items.

16 Claims, 3 Drawing Sheets

FOOD ITEM GRADING

CROSS-REFERENCE TO RELATED APPLICATIONS

This application claims priority to and benefit of U.S. Provisional Application Ser. No. 61/106,487 filed Oct. 17, 2008; U.S. Provisional Application Ser. No. 61/109,868 filed Oct. 30, 2008; and U.S. Provisional Application Ser. No. 61/251,692 filed Oct. 14, 2009. The above provisional patent applications are hereby incorporated herein by reference.

BACKGROUND

1. Field of the Invention

Embodiments of the invention are in the field of grading of food items based on nutritional and other factors.

2. Related Art

Food nutritional information is commonly provided on food packaging. For example, a food label may indicate the serving size, grams of protein and carbohydrates, and ingredients of a food item. The number of different pieces of information provided for a food item can make it difficult to compare different food products.

SUMMARY

A computer based system is configured for providing relative scores (e.g., grades) to food items or lists of food items. These scores are based on multiple inputs such as nutritional data, caloric content, ingredients, portion sizes and a user profile. The user profile may include information customized by the user, such as one or more medical states, food allergies, nutritional and caloric goals, weight, age, and/or the like. The customizable user profile allows the scoring of food items or lists of food items to be made on a user specific basis. For example, the score given to a food item may be based on how well the characteristics of that food item match the user's needs as represented by their user profile.

The scoring of a food item optionally includes the treatment of some nutritional data as a Boolean value to produce a binary (yes or no) result. This treatment may be used for ingredients for which no quantitative information is available. For example, if a food item includes peanuts this information may be used as to produce a binary result as part of calculating a score.

The scoring of a food item optionally includes the treatment of some nutritional data as a quantitative value to produce a quantitative result. This treatment is used for data for which quantitative information is available. For example, a food item including 200 mg of sodium may receive a different score than a food item including 600 mg of sodium.

The scoring of a food item may include the comparison of multiple quantitative and/or multiple binary values to nutritional preferences included within a user profile. These nutritional preferences may be selected based on a medical state of the user, individually entered by a user, based on a default value, and/or calculated. For example, caloric targets may be calculated based on a user's weight, height and age. In some embodiments, the scoring of a food item includes the use of multi-variable linear equation in which nutritional data is multiplied by coefficients, the coefficients being based on a user profile.

The relative scores provided for food items are configured such that different food items can be compared on a single measure. This greatly simplifies the comparison of different foods relative to the prior art. Some embodiments of the invention include a system in which a user can select a food item and compare the score of that item (based on their customized profile) with the scores of other food times within a same category. A user's food item selections are optionally saved to a food item list, e.g., a shopping list. In some embodiments a relative score can be calculated for a shopping list. This score takes into account multiple food items within the list and may reflect the nutritional balance of the list as a whole. The user may observer how removing or adding specific items to the list changes the list's score.

In some embodiments, the systems and method of the invention take into account that a food item or list may be shared among several people. Each of these people may have a different user profile, e.g., different nutritional preferences, their score for the same food item may, therefore, be different.

Various embodiments of the invention include a computing system comprising a processor memory and logic. The memory is configured to store a user profile customized by a user and configured to store food nutritional data on a plurality of food items. The food nutritional data includes multiple nutritional values for each food item. The logic includes computing instructions configured to execute on the processor and to generate a relative score for each of the plurality of food items based on the multiple nutritional values and the user profile; computing instructions configured to present the relative scores for more than one of the food items to the user; computing instructions configured to receive a selection of one of the more than one food items from the user; and computing instructions configured to store the selection in a list associated with the user profile.

Various embodiments of the invention include a method of providing a grade for a food item to a user. This method comprises identifying the food item, e.g., by receiving the identification from a user or determining that the food item is a member of a food category. Multiple nutritional values characterizing the food item are then retrieved from a digital storage device such as a hard drive and/or a database. The method further includes receiving a user profile characterizing nutritional preferences of a user and using a processor to calculate a grade for the food item based on the nutritional values and the user profile. This calculation optionally includes calculating a binary score for the food item based on a Boolean value of the nutritional values and the nutritional preferences, and calculating a non-binary score for the food item based on more than one of the nutritional values and the nutritional preferences. The binary and/or non-binary score are used to calculate a grade (e.g. a normalized score) for the food item. This grade is optionally provided to the user.

Various embodiments of the invention include a method of comparing food items. This method comprises identifying a first food item and a second food item. Based on these identities multiple nutritional values characterizing each of the first food item and the second food item are retrieved from a storage device. The method further includes receiving a user profile characterizing nutritional preferences customized by a user. The user profile and the multiple nutritional values are then used to calculate a first grade for the first food item and a second grade for the second food item, based on the nutritional preferences and the multiple nutritional values for the first food item and second food item, respectively. The first grade and the second grade are then optionally provided to the user, e.g., through a browser interface.

DETAILED DESCRIPTION

Figure 1:
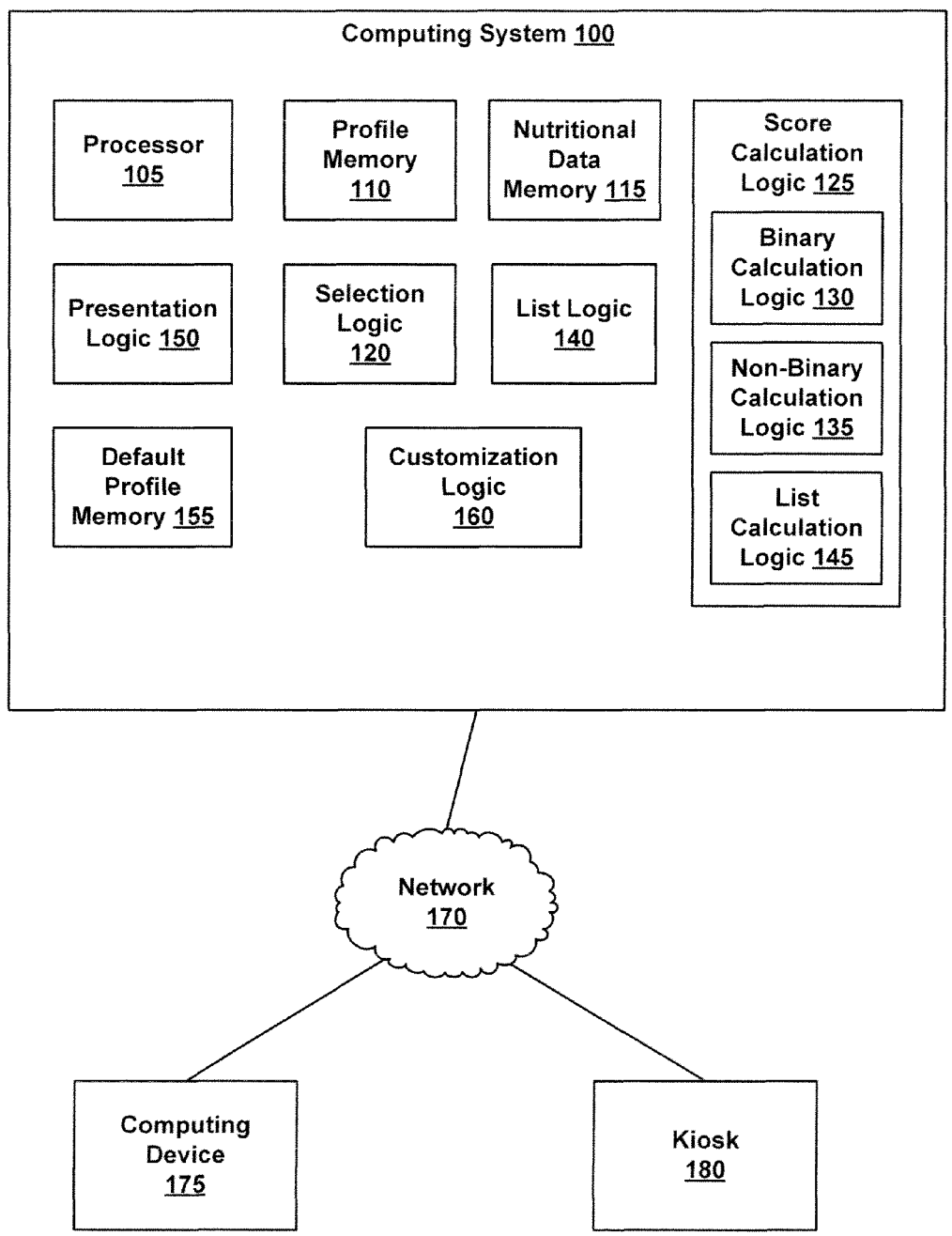
FIG. 1 is a block diagram illustrating a computing system, according to various embodiments of the invention.

FIG. 1 is a block diagram illustrating a Computing System 100, according to various embodiments of the invention. Computing System 100 may include a personal computer, a server, a web server, a file server, a distributed computing system connected by a network, a communication device, and/or the like. In some embodiments, Computing System 100 is configured to be accessed over a Network 170. Network 170 may be the internet, a telephone network, a computer network, a local area network, and/or the like. Optionally, Network 170 is configured for communication via IP/TCP protocols. Computing System 100 may be accessed using a Computing Device 175, such as a user's personal computer, cellular phone, personal digital assistant, telephone, or the like. Computing Device 175 is optionally configured to execute a browser such as Internet Explorer™ or FireFox™ and communicate with Computing System 100 via this browser. Computing System 100 may also be accessed using a Kiosk 180. Kiosk 180 is optionally located within grocery store.

Computing System 100 comprises at least one Processor 105. Processor 105 includes a microprocessor, an ASIC, a programmable logic array, a communication circuit, a central processing unit, and/or the like. Processor 105 is typically configured to perform specific tasks by the addition of software and/or firmware. For example, Processor 105 may be configured to execute the logic discussed herein.

Computing System 100 further includes a Profile Memory 110 configured to store a user profile. Profile Memory 110 may include random access memory, static memory, non-volatile memory, volatile memory, a hard drive, an optical drive, magnetic media, optical media, and/or other digital storage devices. Profile Memory 110 is optionally configured to store a database of profiles associated with a plurality of users. The user profiles include user identification information such as a user login name, a user's name, an identification number, an account name, a password, and/or the like.

The user profiles further include medical information regarding the user and/or nutritional preferences of the user. This medical information may be provided by a user or a doctor via a browser. For example, the user profile may include information that the user has the medical states of type II diabetes, hypertension and an allergy to shellfish, and/or the user profile may include information such as the user's age, gender, height and weight, activity level, genetic information, etc. Any of the above information can be considered part of the medical state. Medical states are optionally indicated using standard diagnosis codes. The user profile may include nutritional preferences such as a vegetarian diet, a kosher practice, a desire to avoid certain preservatives or other ingredients, a desire to increase or reduce certain dietary components, and/or the like. For example, a user may add to their profile that they wish to avoid foods including high fructose corn syrup or foods with a high glycemic index. Nutritional preferences can be binary or non-binary preferences. For example, a need to avoid peanut products can be represented using a binary value, such that products including peanuts are absolutely avoided. In contrast, a preference to avoid lactose may be expressed on a multi-value (non-binary) value. In some embodiments, multi-value preferences are represented by a sliding scale, or a 1 to 5 rating. A user that has limited tolerance for lactose my represent their preference with a low rating. In some embodiments, a user may chose between representing a nutritional preference as a binary value (expressing an absolute preference) or a multi-value value (expressing a non-absolute preference).

The user profile may also include multi-dimensional information. For example, total carbohydrates may be represented as a vector having dimensions of "sugars," "dietary fiber" and "alcohol sugars." Likewise, calories may be represented as a vector having dimensions of calories received as fat, protein, carbohydrates, etc. Other nutritional information that can be multi-dimension include fat ("saturated," "trans fat," polyunsaturated," etc.), nutrients (vitamins A, C, B12, . . . , calcium, iron, sodium, etc.), or the like.

User profiles stored in Profile Memory 110 are optionally grouped in profile "families." Profile families may be used to generate multiple grades for a food item in response to a single request from a user. For example, a profile family may include profiles of four people who eat in the same household. Each of these people can have different medical states and/or nutritional preferences. As such the score generated for the food item may be different for each user. In some embodiments an average score can be provided representing how the food item scores for the entire profile family.

Computing System 100 further includes Nutritional Data Memory 115 configured to store food nutritional data regarding a plurality of food items. This food nutritional data typically includes food item identification information as well as multiple nutritional values for each food item. For example, the nutritional values may include a serving size, a number of servings per container, a glycemic index, an amount of fat, an amount of cholesterol, an amount of sodium, an amount of carbohydrates, an amount of protein, and/or the like. The nutritional values may also include amounts of various vitamins and minerals. The nutritional values may include Boolean or non-Boolean (e.g., quantitative) values. Examples of Boolean values include the presence of ingredients for which no quantitative information is available. The nutritional data stored in Nutritional Data Memory 115 optionally includes the information provided on the U.S. Food and Drug Administration "Nutrition Facts Label" for packaged foods.

The food items are optionally identified using a universal product code or numeric codes used to identify fruits and vegetables. The food items can be processed or fresh. Some food nutritional data is optionally stored external to Computing System 100, for example at a website of a manufacturer. Nutritional Data Memory 115 may include random access memory, static memory, non-volatile memory, volatile memory, a hard drive, an optical drive, magnetic media, optical media, and/or other digital storage devices.

Computing System 100 further includes Selection Logic 120 configured for the selection of a specific food item. In some embodiments, Selection Logic 120 includes computer code configured to present a web interface to a user within a browser. A user may select a food item from a list of items, may select a food category and be presented with a list of food items within that category, may enter a food item and be presented with one or more alternatives to that food item, and/or may enter a search term and be presented with relevant food items.

Computing System 100 further includes Score Calculation Logic 125 configured to calculate a score for one or more food items. This calculation is based on the food nutritional data stored in Nutritional Data Memory 115 and a profile of a user. The score represents a conglomeration of the nutritional information available for a food item as a function of the user profile. In various embodiments, there are a wide variety of methods by which a score can be calculated. In some embodiments an equation (e.g., a linear equation) is used that includes nutritional values multiplied by coefficients. The coefficients are based on information such as nutritional preferences or a medical state included in the user profile.

The score calculated using Score Calculation Logic 125 is typically configured for comparing food items and to show a user which food item better matches their user profile, e.g, are healthier or otherwise more desirable. Score Calculation Logic 125 is optionally configured to calculate a grade based on a score. A grade is a representation of a score normalized to a grading scale such as A to F, 1 to 10, one star to five stars, "Very Good" to "Very Bad," etc.

Score Calculation Logic 125 optionally includes a Binary Calculation Logic 130 and a Non-Binary Calculation Logic 135. Binary Calculation Logic 130 is configured to calculate a score based on binary nutritional values, such as the presence of a particular ingredient. For example, a user profile may include an indication that the user is very allergic to peanuts and a food item may include peanuts or be manufactured in a place that processes peanuts. In this case, a binary score of zero may be calculated indicating that the food item is very undesirable. Binary Calculation Logic 130 may use Boolean logic. Binary Calculation Logic 130 is typically used to dramatically lower scores for food ingredients that are absolutely to be avoided.

Non-Binary Calculation Logic 135 is configured to calculate a score based on quantitative information within the nutritional data and the user profile. For example, the calculation of a score may include multiplying an amount of sodium included in a food item by a coefficient based on the user profile. The coefficient can be positive or negative. For example, a user having a medical state including "hypertension" may have a negative coefficient for sodium such that food items including relatively high amounts of sodium are given relatively lower scores. Likewise, some medical states result in a positive coefficient for dietary fiber such that food items having relatively high amounts of fiber are give relatively higher scores.

Non-Binary Calculation Logic 135 is optionally configured to calculate scores based on nutritional preferences treated as a vector. For example, as discussed elsewhere herein, the calories of a food item may be represented by a vector including components for different sources of the calories (e.g., fat, protein, carbohydrates, etc.). In some embodiments, a vector is multiplied by a vector of coefficients to generate a score. In some embodiments, the distance between a nutritional preferences vector and an "ideal" vector is calculated. For example, the distance between an ideal caloric vector and a caloric vector of a food item may be used to calculate a score. Some calculations include both multiplication by a coefficient vector and calculation of a distance from an ideal vector. Such calculations are performed using well know methods of vector manipulation.

Non-Binary Calculation Logic 135 is optionally configured to calculate scores based on a user experience regarding a food item. The user experience relates to the user's desire to eat the food item, e.g., do they like the food item. A user experience may be determined, for example, by having a user indicate their particular likes and dislikes regarding food, may be based on reviews of a food item from a plurality of users, and/or may be based on the likes and dislikes of members of a user's social network or friends.

Score Calculation Logic 125 is optionally configured to combine a binary and a non-binary score to produce an overall score for a food item. This combination may include a Boolean operation or a multiplication step. In some embodiments a zero or negative binary score will result in a zero or negative overall score. As such, the presence of peanuts in a food item will result in a very low score for a user who has indicated a nutrition preference including no peanuts.

Score Calculation Logic 125 optionally includes List Calculation Logic 145 configured to calculate a score for a list of food items. This score may be calculated by combining scores of each food item or, alternatively, this score may be calculated by calculating a score from scratch based on the combined nutritional data of the food items in the list and the user profile. For example, in some embodiments a score for a list is calculated by just taking an average of each individual item score. This averaging may be weighted by an amount of each food item purchased and/or a serving size. Calculating a score based on the combined nutritional data of each food item in a list can have the advantage that nutritional balance is better represented by the score. The combined nutritional data can be represented by a vector or vectors that are the sum of corresponding vectors (e.g., caloric vector, nutrient vector, carbohydrate vector, fat vector, etc.) for each of the food items. The sums produce vectors that represent the caloric content, nutrients, etc. of the combination of items on the list. These vectors are then compared with ideal vectors, (which may be dependent on a medical state). Regardless of how the score of a list of food items is calculated, in typically embodiments, a user can add or subtract food items from the list to observe how they affect the list score. This process is optionally performed via a browser.

Computing System 100 typically includes Presentation Logic 150 configured to provide scores and or grades to a user, to allow a user to select food items, to allow a user to manage a list of food items, and/or for a user to customize their user profile. In typical embodiments, Presentation Logic 150 is configured to generate computing instructions (e.g., html, xml, scripts, java, or the like) configured to present an interface to a user within a browser. Alternatively, Presentation Logic 150 is configured to present information to a user via a software agent. Part of Presentation Logic 150 is optionally disposed on Computing Device 175 or Kiosk 180.

Presentation Logic 150 is typically configured to receive inputs from a user. These inputs may include selections of food items, commands to print lists, customization of a user profile, search terms, and/or the like. For example, in some embodiments, Presentation Logic 150 is configured to present a search field to a user through a browser. The search field is configured for a user to search for a food item by grade, by category, by name, by UPC, by text, and/or the like.

Computer System 100 typically includes Default Profile Memory 155 configured to store one or more default profile. These default profiles may be associated with one or more medical states. For example, there may be a default profile for type II diabetes, a default profile for type II diabetes combined with hypertension, a default profile associated with a specific age group, a default profile associated with obesity, etc. Default profiles are determined based on current understandings of the nutritional needs of people with specific medical states, age, weight, genetic history, etc.

Default profiles are optionally used as the starting point for a user's profile based on the user's indication of one or more medical states. For example, a user may first provide Computing System 100 with information such as age, height, weight, medical history, current medical states, genetic profile, goals, and or the like. This information is used to retrieve one or more default profiles from Default Profile Memory 155. More than one default profile may be retrieved when, for example, the user provides more than one medical state.

These default profiles are combined into a single user profile, e.g., by averaging and/or Boolean logic, to produce a single profile for the user. The methods by which profiles are combined depend on the specific medical states. For example, a food allergy may be directly copied from a default profile to a user profile, while a recommended vitamin B12 intake may be averaged from several default profiles. The user profile is stored in Profile Memory 110 in association with the user. The user may then further customize their profile.

Computing System 100 further typically includes Customization Logic 160 configured for a user to customize (edit) their user profile. This customization may include indication of nutritional preferences, medical states, caloric targets, personal data, or anything else included in the user's profile. For example, a user who wishes to lose weight may adjust caloric targets based on a target rate of weight loss. Customization optionally includes association of a user profile with other user profiles to form a profile family. In some embodiments, any of the information stored in a user's profile can be customized by the user.

Figure 2:
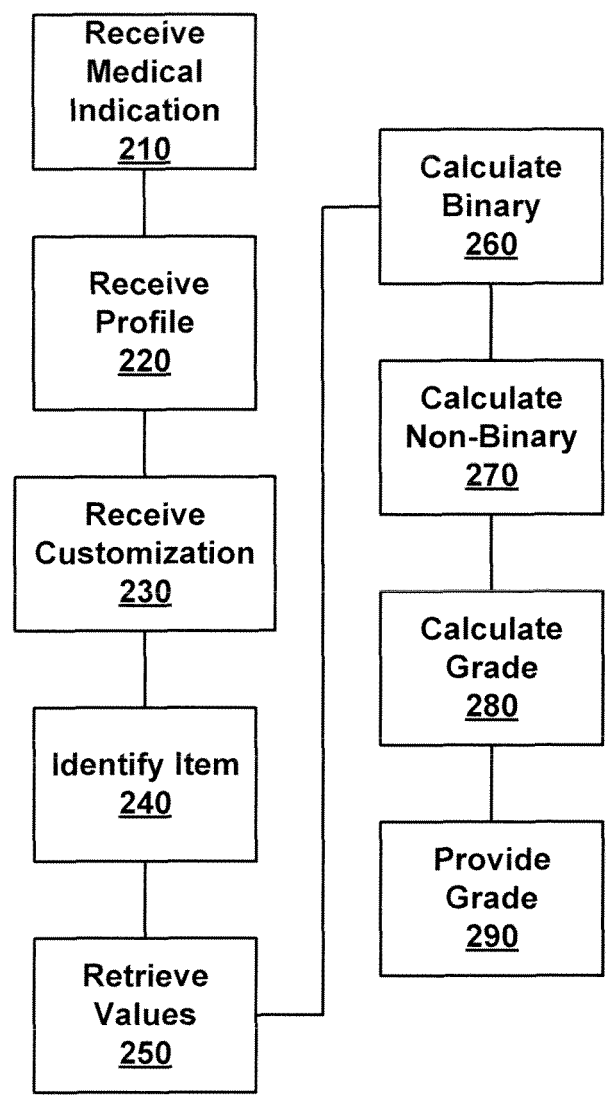
FIG. 2 is an illustration of a method of providing a grade for a food item to a user, according to various embodiments of the invention.

FIG. 2 is an illustration of a method of providing a grade for a food item to a user, according to various embodiments of the invention. The grade is based on nutritional information about the food item and a profile of the user. The method illustrated in FIG. 2 is optionally performed using the Computing System 100 and can be performed in alternative orders.

In an optional Receive Medical Indication Step 210 an indication of a medical state of a user is received by Computing System 100. This indication is optionally received via a browser and may include the user selecting from among a plurality of medical states in a menu. The medical state may include a disease or other condition for which diet is important. Several examples of medical states are discussed elsewhere herein. The received indication is stored in Profile Memory 110 in association with the user.

In an optional Receive Profile Step 220 one or more default profile is received from Default Profile Memory 155. The default profile is selected from among a plurality of default profiles stored in Default Profile 155. This selection may be based on characteristics of the user such as their age, height, weight, gender, genetic information, etc. In some embodiments the default profile selected based on one or more medical state received in Receive Medical Indication Step 210. For example, a received default profile may be associated with a specific medical state. As discussed elsewhere herein, the received default profile may be combined with other profiles, and is saved in Profile Memory 110 as the user's profile.

In an optional Receive Customization Step 230 Computing System 100 receives a customization of the user's profile. This customization is typically under the direction of the user or a caretaker (e.g., doctor) of the user. In some embodiments, the received customization may include modification of any of the nutritional preferences or other information that can be stored in the profile of the user. The customization may be received over Network 170 from Computing Device 175 or Kiosk 180.

Receive Profile Step 210, Receive Medical Indication Step 220 and/or Customization Step 230 are optional in instance where a profile for the user is already available.

In an Identify Item Step 240 a food item is identified. This identification may include the selection of the food item by the user from a list of food items, the user providing an identifier of the food item (e.g., a UPC), or the identification by Computing System 100 of food items within a same category as another food item. For example, in some embodiments, Identify Item Step 240 includes searching Nutritional Data Memory 115 for a food item in a specific category or for a food item that is a potential substitute for another food item.

In a Retrieve Values Step 250 multiple nutritional values characterizing the food item identified in Identify Item Step 240 are retrieved from Nutritional Data Memory 115. This retrieval is optionally accomplished using a database query. The nutritional values may include ingredients, information from a nutritional label, or other nutritional information discussed herein.

In an optional Calculate Binary Step 260 a binary score for the food item identified in Identify Item Step 240 is calculated using Binary Calculation Logic 130. This calculation is based on the profile of the user customized in Receive Customization Step 240 and on one or more of the nutritional values retrieved in Retrieve Values Step 250. As discussed elsewhere herein, the calculation of a binary score optionally includes the use of Boolean operations.

In a Calculate Non-Binary Step 270 a non-binary score for the food item identified in Identify Item Step 240 is calculated using Non-Binary Calculation Logic 135. This calculation is based on the profile of the user customized in Receive Customization Step 240 and on one or more of the nutritional values retrieved in Retrieve Values Step 250. Calculate Non-Binary Step 270 optionally includes the comparison of vectors representing nutritional values of the food item with an ideal vector. For example, in some embodiments, the distance between a vector representing the minerals and vitamins of the food item and a vector representing mineral and vitamin targets of the user profile is calculated.

In an optional Calculate Grade Step 290 a grade is calculated from the binary score calculated in Calculate Binary Step 260 and/or the non-binary score calculated in Calculate Non-Binary Step 270. This grade is relative to a grading scale and, as such, is configured for comparison with grades calculated for other food items. The calculated grade is intended to represent how well the food item matches the preferences of the user, e.g., how nutritious or healthy the food item is for the user. In some embodiments, the binary and non-binary scores are combined without normalization to a grade.

In a Provide Grade Step 290 the grade calculated in Calculate Grade Step 290, the binary score calculated in Calculate Binary Step 260, the non-binary score calculated in Calculate Non-Binary Step 270, and/or a combination thereof is provided to the user. This information is provided using Presentation Logic 150 and is optionally provided via Network 170 to Computing Device 175 or Kiosk 180. For example, the information may be displayed on a browser within Computing Device 175. In some embodiments, grades or scores for multiple food items are displayed together for comparison by the user. These multiple food items may be in the same food category.

Figure 3:
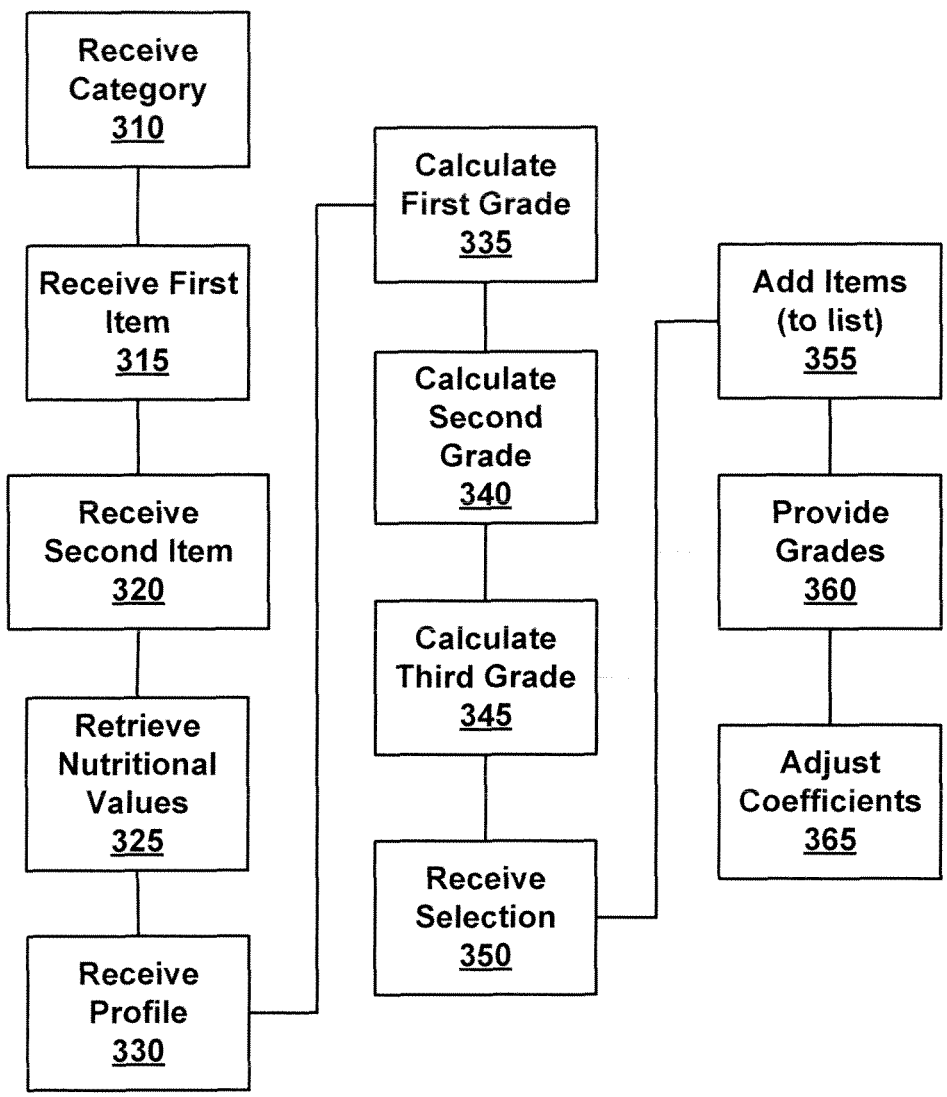
FIG. 3 is an illustration of a method of comparing food items, according to various embodiments of the invention.

FIG. 3 is an illustration of a method of comparing food items, according to various embodiments of the invention. In this method grades for several food items are calculated and provided to a user for comparison. The methods illustrated by FIG. 3 are optionally performed using Computing System 100. The steps illustrated in FIG. 3 may be performed in a wide variety of alternative orders.

In an optional Receive Category Step 310 a food item category is received by Computing System 100. The food item category may be received by the selection of a category by a user. Alternatively the food item category may be received as a result of a food item selection by a user and a determination of which category(ies) the selected food item is in.

A food item category is a grouping of food by type. For example, in some embodiments, various categories include "Crackers," "Jellies/Jams," "Beer," "Spices," "Kosher," "Vegetarian," "Desserts," "Meat," "Breads," etc. Any classification that can optionally be used to group food items can be used as a food item category. Some embodiments provide the ability for a user to define custom categories. Some categories include food items that can be substituted for each other. For example, a "Snack Bar" category may include various alternative snack bars. In some embodiments categories are organized by nutrition experts to specifically include healthier alternatives to commonly eaten foods.

In a Receive First Item Step 315 a first food item selection is received by Computing System 100. In a Receive Second Item Step 320 a second food item selection is received by Computing System 100. The selection of the first and second food items may be the result of a user selecting specific item(s) and/or may be the result of a search of Nutritional Data Memory 115 for one or more food items within the food category received in Receive Category Step 310. In one example, a user selects the first food item and the second food item is automatically selected by Computing System 100 as a member of a same food category as the first food item. In another example, the first and second food items are both automatically selected by Computing System 100 based on their membership within the food category received in Receive Category step 310. In another example, both the first and second food items are selected from a list of food items provided to the user by Presentation Logic 150. In another example, one or both of the first and second food items are selected as a result of the user providing a UPC or other food item identifier. In some embodiments, a user can designated that a selected food item, or some fraction of a selected food item is designated for a particular member of a group, e.g., for a particular member of a family. For example, the user may designate that ½ the ice cream is for dad, the cereal should be divided equally among dad and mom, that the bran muffins are for grandma, and that none of the beer is for the baby.

In a Retrieve Nutritional Values Step 325 nutritional values for the first and second food items, selected in Receive First Item Step 315 and Receive Second Item Step 320, are retrieved from Nutritional Data Memory 115. As is discussed elsewhere herein, the retrieved nutritional values may include a wide variety of information, including binary and/or non-binary values. In some embodiments, Retrieve Nutritional Values Step 325 includes execution of a query on Nutritional Data Memory 115. In some embodiments, Retrieve Nutritional Values Step 325 includes accessing a food manufacturer website or other external data source.

In a Receive Profile Step 330 one or more user profile are received. This profile or these profiles are typically received from Profile Memory 110. However, in alternative embodiments, a profile may be received directly from Default Profile Memory 155, e.g., if no user has been identified or if no profile for a user yet exists. Alternatively, the profile may be received directly from the user.

In a Calculate First Grade Step 335 Score Calculation Logic 125 is used to calculate a grade, or score, for the first food item whose selection is received in Receive First Item Step 315. In an optional Calculate Second Grade Step 340 Score Calculation Logic 125 is used to calculate a grade, or score, for the second food item whose selection is received in Receive Second Item Step 320.

In an optional Calculate Third Grade Step 345 a third grade or score is calculated using Score Calculation Logic 125. This grade or score is a combined grade or score representative of both the first item and the second item in combination. For example, the third grade or score may be representative of a food item list of which the first and second items are members. As discussed elsewhere herein, the third score or grade may be calculated by averaging the scores/grades for the first and second food items or by calculating a grade directly based on the user profile and nutritional values.

The calculations in Calculate First Grade Step 335, Calculate Second Grade Step 340, and Calculate Third Grade Step 350 may be performed using the various approaches discussed elsewhere herein. These calculations are based on the user profile and nutritional values retrieved from Nutritional Data memory 115. The calculations in Calculate First Grade Step 335, Calculate Second Grade Step 340, and Calculate Third Grade Step 350 optionally include the calculation of grades based on more than one user profile that are members of the same profile family. For example, a first, a second and/or a third grade may be calculated for each member of a family based on their individual user profiles. The third grade may represent a combination of grades for different members of the family. The calculation of grades is optionally dependant on a designation received from the user as to how food items are to be divided among the group. For example, it may be designated that the bran muffin is for grandma and that none of the beer is for the baby. These designations, if available, are taken into account when calculating grades.

An optional Receive Selection Step 350, an optional Add Items Step 335 and an optional Provide Grades Step 360 may be performed in any order. For example, in some embodiments, Provide Grades Step 360 is performed prior to Receive Selection Step 350. This allows a user to make the selection in response to the grades provided in Provide Grades Step 360. Alternatively, Provide Grades Step 360 may occur both before Receive Selection Step 350 and following Add Item Step 355. This allows a user to first select a food item and then view how that food item affects the grade or score for a food item list.

Receive Selection Step 350 includes receiving a selection between the first food item and the second food item from the user. This selection is typically received under the control of Presentation Logic 150 and may be received by Network 170 form Computing Device 175 or Kiosk 180. In some embodiments, the selection is made by the user in response to considering the grades or scores calculated in previous steps.

In an Add Items Step 355 a food item selected by the user, e.g., in Receive Selection step 350, is added to a food item list, such as a shopping list. Calculate Third Grade Step 354 is optionally used to calculate an overall grade for this food item list. The food item list is optionally stored in Profile Memory 110 in association with the user's profile. For example, the user profile may include a log of past shopping lists.

In Provide Grades Step 360 the grades calculated in Steps 335, 340 and/or 345 are presented to the user using Presentation Logic 150. This presentation optionally includes controls configured to allow a user to select from among the food items, request grades for additional food items, add a food item to a food item list, print a shopping list, save a shopping list, and/or the like. In some embodiments, food items are presented ranked by their grades or scores.

In an optional Adjust Coefficients Step 365 coefficients used by Score Calculation Logic 125 are adjusted based on the contents of a food item list. As a result, scores for additional food items are adjusted for food items already included in the food item list. For example, if a banana receives a first score the first time it is added to a food item list, the fiftieth banana added to the list will receive a lower score because of coefficient adjustment. This reflects the fact that a diet of purely bananas may not be as good nutritionally relative to a more diverse diet. More specifically, if a food item list already includes an abundance of potassium, trans fats, or protein, then coefficients for these items may be reduced so that further food items would have to have reduced amounts of these items in order to score well. The coefficients are modified in order to achieve a more diverse diet. The adjustment of coefficients may be determined based on default profiles and the medical states of a user.

Several embodiments are specifically illustrated and/or described herein. However, it will be appreciated that modifications and variations are covered by the above teachings and within the scope of the appended claims without departing from the spirit and intended scope thereof. For example, while the current disclosure is directed at food items, alternative embodiments of the invention may be applied to other multi-component products such as vehicles or computers. The systems and methods described herein may be applied to animal diets. A cost (purchase price) preference is optionally included in a user profile. This cost preference may be combined with a cost of the food item stored in Nutritional Data Memory 115 and may be used in calculating scores or grades for food items.

The various examples of logic noted above can comprise hardware, firmware, or software stored on a computer-readable medium, or combinations thereof. This logic may be implemented in an electronic device to produce a special purpose computing system. A computer-readable medium, as used herein, expressly excludes paper. Computer-implemented steps of the methods noted herein can comprise a set of instructions stored on a computer-readable medium that when executed cause the computing system to perform the steps. A computing system programmed to perform particular functions pursuant to instructions from program software is a special purpose computing system for performing those particular functions. Data that is manipulated by a special purpose computing system while performing those particular functions is at least electronically saved in buffers of the computing system, physically changing the special purpose computing system from one state to the next with each change to the stored data.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

The invention claimed is:

1. A method of providing a grade for a food item to a user, the method comprising:
    identifying the food item;
    retrieving multiple nutritional values characterizing the food item, from a digital storage device;
    receiving a user profile characterizing nutritional preferences of a user;
    calculating a binary score for the food item based on a Boolean value of the nutritional values and the nutritional preferences, using a processor;
    calculating a non-binary score for the food item based on more than one of the nutritional values and the nutritional preferences;
    calculating a grade for the food item based on the binary score and the non-binary score; and
    providing the grade to the user.

2. The method of claim 1, wherein identifying the food item includes receiving a universal product code from the user.

3. The method of claim 1, wherein identifying the food item includes receiving a food category selection from the user.

4. The method of claim 1, wherein identifying the food item includes identifying food items in a same category as a food item selected by the user.

5. The method of claim 1, wherein the food item is identified using a bar code.

6. The method of claim 1, wherein calculating the non-binary score includes using a model of the healthiness of the food item, the model including a set of coefficients by which the multiple nutritional values are multiplied.

7. The method of claim 6, wherein some of the coefficients are negative and some of the coefficients are positive.

8. The method of claim 6, wherein the set of coefficients are selected by a medical indication.

9. The method of claim 8, wherein the medical indication is one of celiac disease, type II diabetes, high blood pressure, lactose intolerance or obesity.

10. The method of claim 6, wherein the set of coefficients are customized by the user.

11. The method of claim 6, wherein the set of coefficients are based on previously selected food items.

12. The method of claim 1, wherein calculating the non-binary score includes comparing a caloric content of the food item with a target caloric value, the target caloric value being based on the user profile.

13. The method of claim 1, wherein calculating the binary score includes using a set of user selected coefficients and the nutritional values, the user selected coefficients being configured to indicate a food allergy, a vegetarian diet, a vegan diet, lactose intolerance, or a desire to avoid a particular food ingredient.

14. The method of claim 1, wherein the grade is provided to the user via a browser executing on a client computer.

15. The method of claim 1, further comprising receiving a customization of the nutritional preferences from the user.

16. The method of claim 1, further comprising receiving a medical indication from the user and using the medical indication to set a default user profile for the user.

* * * * *